(12) United States Patent
Poustka et al.

(10) Patent No.: US 6,312,688 B1
(45) Date of Patent: Nov. 6, 2001

(54) TYROSINE-PHOSPHATASE-RELATED PROTEIN

(75) Inventors: Annemarie Poustka, Heidelberg; Petra Kioschis, Heddesheim, both of (DE); Jocelyn Laporte, Strassburg (FR); Ling Jia Hu, Denver, CO (US); Jean Louis Mandel, Illkirch Cédex (FR); Niklas Dahl, Uppsala (SE)

(73) Assignees: Deutsches Krebsotorschungszentrum Stiftung des Offentlichen Rechts,, Heidelberg (DE); Institut National de la Sante et de la Recherche Medicale, Paris (FR)

( * ) Notice: Subject to any disclaimer, the term of this patent is extended or adjusted under 35 U.S.C. 154(b) by 0 days.

(21) Appl. No.: 09/155,078
(22) PCT Filed: Mar. 21, 1997
(86) PCT No.: PCT/DE97/00592
§ 371 Date: Mar. 2, 1999
§ 102(e) Date: Mar. 2, 1999
(87) PCT Pub. No.: WO97/35015
PCT Pub. Date: Sep. 25, 1997

(30) Foreign Application Priority Data

Mar. 21, 1996 (DE) .............................. 196 11 234

(51) Int. Cl.⁷ .......................... A61K 38/46; A61K 38/00; C12N 9/16; C12N 1/20; C12N 15/00
(52) U.S. Cl. .......................... 424/94.5; 435/196; 435/325; 435/252.3; 435/320.1; 536/23.2; 514/12; 514/44
(58) Field of Search ............................. 435/69.1, 320.1, 435/325, 252.3, 196, 6; 514/12, 44; 424/94.5

(56) References Cited

PUBLICATIONS

Laporte et al., Nature Genet., 13, 175–182, May 1996.*

Mackenzie et al., J.B.C., 265(15), 8699–8703, May 1990.*

* cited by examiner

*Primary Examiner*—Ponnathapu Achutamurthy
*Assistant Examiner*—Maryam Monshipouri
(74) *Attorney, Agent, or Firm*—Burns, Doane, Swecker & Mathis, L.L.P.

(57) ABSTRACT

The present invention relates to a tyrosine-phosphatase-related protein, a DNA which codes for such a protein and a process for producing such a protein. In addition, the invention concerns the use of the DNA and protein and antibodies directed against the protein.

9 Claims, 5 Drawing Sheets

Fig. 1A

```
  1 GCAGCCCGAGCAGCCTGGCAACGGGCGGTGCGCCCGAGCCCGAGAGTTTCCAGGATGGCT
  1  A  A  E  Q  P  G  N  G  G  A  R  S  P  R  V  S  R  M  A

61 TCTGCATCAACTTCTAAATATAATTCACACTCCTTGGAGAATGAGTCTATTAAGAGGACG
 21  S  A  S  T  S  K  Y  N  S  H  S  L  E  N  E  S  I  K  R  T

121 TCTCGAGATGGAGTCAATGAGATCTCACTGAGGCTGTTCCTGACTTCCAGGAGAAACA
 41  S  R  D  G  V  N  R  D  L  T  E  A  V  P  R  L  P  G  E  T

181 CTAATCACTGACAAAGAAGTTATTTACATATGTCCTTTCAATGGCCCCATTAAGGGAAGA
 61  L  I  T  D  K  E  V  I  Y  I  C  P  F  N  G  P  I  K  G  R

241 GTTTACATCACAAATTATCGTCTTTATTTAAGAAGTTTGGAAACGGATTCTTCTAATA
 81  V  Y  I  T  N  Y  R  L  Y  L  R  S  L  E  T  D  S  S  L  I

301 CTTGATGTTCCTCTGGGTGTGATCTCGAGAATTGAAAAAAATGGGAGGCGCAAGTAGA
101  L  D  V  P  L  G  V  I  S  R  I  E  K  M  G  G  A  T  S  R

361 GGAGAAAATTCCTAGATGGTCTAGATATTACTTGTAAAGACATGAGAAACCTGAGGTTCGCT
121  G  E  N  S  Y  G  L  D  I  T  C  K  D  M  R  N  L  R  F  A

421 TTGAAACAGGAAGGCCACAGCAGAAGAGATATGTTTGAGATCCTCACGAGATACGCGTTT
141  L  K  Q  E  G  H  S  R  R  D  M  F  E  I  L  T  R  Y  A  F

481 CCCCTGGCTCACAGTCTGCCATTATTTGCATTTTTAAATGAAGAAAAGTTTAACGTGGAT
161  P  L  A  H  S  L  P  L  F  A  F  L  N  E  E  K  F  N  V  D
```

Fig. 1B

```
541 GGATGGACAGTTTACAATCCAGTGGAAGAATACAGGAGGCAGGGCTTGCCCAATCACCAT
181  G  W  T  V  Y  N  P  V  E  E  Y  R  R  Q  G  L  P  N  H  H

601 TGGAGAATAACTTTTATTAATAAGTGCTATGAGCTCTGTGACACTTACCCTGCTCTTTTG
201  W  R  I  T  F  I  N  K  C  Y  E  L  C  D  T  Y  P  A  L  L

661 GTGGTTCCGTATCGTGCCTCAGATGATGACCCTCCGGAGAGTTGCAACTTTTAGGTCCGA
221  V  V  P  Y  R  A  S  D  D  D  L  R  R  V  A  T  F  R  S  R

721 AATCGAATTCCAGTGCTGTCATGGATTCATCCAGAAATAAGACGGTCATTGTGCGTTGC
241  N  R  I  P  V  L  S  W  I  H  P  E  N  K  T  V  I  V  R  C

781 AGTCAGCCTCTCTTGTCGGTATGAGTGGGAAACGAAATAAGATGATGAGAAATATCTCGAT
261  S  Q  P  L  V  G  M  S  G  K  R  N  K  D  D  E  K  Y  L  D

841 GTTATCAGGGAGACTAATAAACAAATTTCTAAACTCACCATTTATGATGCAAGACCCAGC
281  V  I  R  E  T  N  K  Q  I  S  K  L  T  I  Y  D  A  R  P  S

901 GTAAATGCAGTGGCCAACAAGGCAACAGGAGGAGGATATGAAAGTGATGATGCATATCAT
301  V  N  A  V  A  N  K  A  T  G  G  G  Y  E  S  D  D  A  Y  H

961 AACGCCGAACTTTTCTTCTTTAGACATTCATAATATTCATGTTATGCGGAATCTTTAAAA
321  N  A  E  L  F  F  L  D  I  H  N  I  H  V  M  R  E  S  L  K
```

Fig. 1C

```
1021 AAAGTGAAGGACATTGTTTATCCTAATGTAGAAGAATCTCATTGGTTGTCCAGTTTGGAG
 341  K  V  K  D  I  V  Y  P  N  V  E  E  S  H  W  L  S  S  L  E

1081 TCTACTCATTGGTTAGAACATATCAAGCTCGTTTTGACAGGAGCCATTCAAGTAGCAGAC
 361  S  T  H  W  L  E  H  I  K  L  V  L  T  G  A  I  Q  V  A  D

1141 AAAGTTTCTTCAGGGAAGAGTTCAGTGCTTCAGTGCATTGCAGTGACGGATGGGACAGGACT
 381  K  V  S  S  G  K  S  S  V  L  V  H  C  S  D  G  W  D  R  T

1201 GCTCAGCTGACATCCTTGGCCATGCTGATGTTGGATAGCTTCTATAGGAGCATTGAAGGG
 401  A  Q  L  T  S  L  A  M  L  M  L  D  S  F  Y  R  S  I  E  G

1261 TTCGAAATACTGGTACAAAAAGAATGGATAAGTTTTGGACATAAATTTGCATCTCGAATA
 421  F  E  I  L  V  Q  K  E  W  I  S  F  G  H  K  F  A  S  R  I

1321 GGTCATGGTGATAAAAACCACCGATGCTGACCGTTCTCCTATTTTTCTCCAGTTTATT
 441  G  H  G  D  K  N  H  T  D  A  D  R  S  P  I  F  L  Q  F  I

1381 GATTGTGTGTGGCAAATGTCAAAACAGTTCCCTACAGCTTTTGAATTCAATGAACAATTT
 461  D  C  V  W  Q  M  S  K  Q  F  P  T  A  F  E  F  N  E  Q  F

1441 TTGATTATAATTTTGGATCATCTGTATAGTTGCCGATTGGTACTTTCTTATTCAACTGT
 481  L  I  I  I  L  D  H  L  Y  S  C  R  F  G  T  F  L  F  N  C

1501 GAATCTGCTCGAGAAAGACAGAAGGTTACAGAAAGGACTGTTTCTTTATGGTCACTGATA
 501  E  S  A  R  E  R  Q  K  V  T  E  R  T  V  S  L  W  S  L  I
```

Fig. 1D

```
1561 AACAGTAATAAAGAAAAATTCAAAAGAAACCCCTTCTATACTAAAGAAATCAATCGAGTTTTA
 521  N  S  N  K  E  K  F  K  N  P  F  Y  T  K  E  I  N  R  V  L

1621 TATCCAGTTGCCAGTATGCGTCACTTGGAACTCTGGGTGAATTACTACATTAGATGGAAC
 541  Y  P  V  A  S  M  R  H  L  E  L  W  V  N  Y  Y  I  R  W  N

1681 CCCAGGATCAAGCAACAACAGCCGAATCCAGTGGAGCAGGTTACATGGAGCTCTTAGCC
 561  P  R  I  K  Q  Q  Q  P  N  P  V  E  Q  R  Y  M  E  L  L  A

1741 TTACGCGACGAATACATAAAGCGGCTTGAGGAACTGCAGCTCGCCAACTCTGCCAAGCTT
 581  L  R  D  E  Y  I  K  R  L  E  E  L  Q  L  A  N  S  A  K  L

1801 TCTGATCCCCCAACTTCACCTTCCCAGTCCTCCTTCGCAAATGATGCCCCATGTGCAAACTCAC
 601  S  D  P  P  T  S  P  S  S  P  S  Q  M  M  P  H  V  Q  T  H

1861 TTCTGAGGGGGACCCTGGCACCCGCATTAGAGCTCGAAATAAAGGCCGATAGCTGACTTTC
 621  F  *

1921 ATTTGGGCATTTGTAAAAGTAGATTAAAATATTTGCCTCCATGTAGAACTTGAACTAA
1981 CATAATCTTAAACTCTTGAATTGTGCCTTCTAGAATACATATTACAAGAAAACTACAGG
2041 GTCCACACGGCAATCAGAAGGAGCTGAGATGAGGTTTTGGAAACCCTGACACCTT
2101 TAAAAAGCAGTTTTTGAAAGACAAAATTTAGATTCTCTTGAGAAATACTATA
2161 TATACAATATATATGGGGGGCTTAATTGAAACAACATTATTTAAAATCAAAGGGGAT
2221 ATATGTTGTGAATGGATTTTCCTGAAGCTGCTTAACAGTTGCTTTGGATTCTCTAAGA
2281 TGAATCCAAATGTGAAAGATGCATGTTACTGCCAAAACCAAATTGAGCTTCAGCTTCCTAG
```

Fig. 1E

```
2341  GCATTACCCAAAAGCAAGGTGTTAAGTAATCATCATGAGTGGTG
2401  ACTTAAGGAGAAATAGCTGTATAGATGAGTTTTCATTATTGGAATTAGGGTAGAA
2461  AATGTTTCCCTAATTTCCAGAGAAGCCTATTTTATATTTTAAAAACTGACAGGG
2521  CCCAGTTAAATATGATTGCATTTTAAATTGCCAGTTTTATTTCTAAATTCTTTCA
2581  TGAGCTTGCCTAAAATTCGGAATGGTTTGTGGCAAACCCCAAAGAGAGCACTG
2641  TCCAAGGATGTCGGGAGCATCCTGCTTAGGGCTTAGGGCTACCGTCTCTAG
2701  TCAGTCCAGCTCATCTGCCAAAATCAGTGCCCCAGAGTACATGTGTGAGCGTATTCTTGAAGT
2761  GAGCATCATCCTTAGAAATCAGTGCCCCAGAGTACATGTGTGAGCGTATTCTTGAAGT
2821  ATTGTGTTTATGCATTTCAATTTCAATTGGTGTTGGCTTCCCCTCCCCACGCGTGC
2881  ATAAAAACTGGTTCTACAAATTTTACTTGAAATTTAAATGCACAGTTCTATCTGAACTA
2941  TTTGTTTTATAGTATTAAGTATATATTTGTAAAGCTCGAGTTAAACAATGAAGTGTTTT
3001  ATTCATTATTAAGTATATATTTGTAAAGCTAACTAATATGGTTTTGTTTTTCAATGAATTAAGAA
3061  ACAATGATTGTAAGGACTATTATAACTAATATGGTTTTGTTTTTCAATGAATTAAGAA
3121  AGATTAAATATCTTTGTAAATTCTTTGTAAATTTTATGTCATAGTTGTAAGTATTTGTAAGTATAAGA
3181  CATCTCAAATACAGTAGTATAATGTATGAATTTGTAAGTATAAATTTATTAGACA
3241  TTCTCTTACTTTTGTAAATGCTGTAAATATTCATAAATAACAAAGTGTCACTCCATA
3301  AAAAGAAAGCTAATAACTAATAGCCTAAAAGATTTTGTGAAATTCATGAAAACTTTTAA
3361  TGGCAATAATGACTAAAGACCTGCTGTAATAAATGTATTAACTGAAACCTAAAAAAAAA
3421  AAAAAAAAA
```

TYROSINE-PHOSPHATASE-RELATED PROTEIN

The present invention relates to a tyrosine-phosphatase-related protein, a DNA which codes for such a protein and a process for producing such a protein. In addition, the invention concerns the use of the DNA and protein and antibodies directed against the protein.

Tyrosine kinase and tyrosine phosphatase are enzymes which have opposite effects. Tyrosine kinase effects the phosphorylation of certain tyrosine residues in proteins, whereas tyrosine phosphatase reverses this phosphorylation again. Both enzymes play an important part for the signal transduction, the control of cell growth and cell differentiation.

Diseases are known which are based on disturbances occurring in Tell differentiation. One of these diseases is myotubular myopathy. It is an X-chromosomal-connected disease which is accompanied by altered muscle cells. This disease manifests itself in general muscle weakness, particularly spontaneous movements are hardly possible. Likewise, the respiration of newborns is strongly confined. This frequently leads to premature death However, the causes of disturbed cell differentiation in the case of myotubular myopathy are not known.

Therefore, it is the object of the present invention to provide a product by which it is possible to investigate the cause of cell differentiation disturbances, particularly in the case of myotubular myopathy, and optionally treat them. According to the invention this is achieved by the subject matters defined in the claims.

Thus, the subject matter of the present invention relates to a tyrosine-phosphatase-related protein, the protein comprising the amino acid sequence of FIG. 1 or an amino acid sequence differing therefrom by one or several amino acids.

The present invention is based on the applicant's finding that a protein exists in animals, particularly mammals, more particularly human beings, which has homologies with known tyrosine phosphatases and also tyrosine phosphatase activity but differs from known tyrosine phosphatases on the DNA level by hybridization under normal conditions. Such a protein has the amino acid sequence of FIG. 1 or an amino acid sequence differing therefrom by one or several amino acids. The applicant has also discovered that the protein is important for cell differentiation. He has found that, in its shortened form and mutated form, respectively, i.e. without or only with restricted tyrosine phosphatase activity, this protein disturbs the differentiation of cells, particularly muscle cells, and more particularly leads to the formation of myotubular myopathy.

The above protein is referred to as "tyrosine-related protein" (TVP) in the present invention.

A further subject matter of the present invention relates to a nucleic acid coding for (TVP). It may be an RNA or a DNA. The latter may be e.g. a genomic DNA or a cDNA. Preferred is a DNA comprising the following:
(a) the DNA of FIG. 1 or a DNA differing therefrom by one or several base pairs,
(b) a DNA hybridizing with the DNA of (a), or
(c) a DNA related to the DNA of (a) or (b) via the degenerated genetic code.

The expression "hybridizing DNA" refers to a DNA which hybridizes with a DNA of (a) under normal conditions, particularly at 20° C. below the melting point of the DNA.

The DNA of FIG. 1 was deposited wit h the DSM (Deutsche Sammlung von Mikroorganismen und Zellkulturen [German-type collection of micro-organisms and cell cultures]) as hp6 under DSM 10558 on Mar. 4, 1996.

A DNA according to the invention is described below in the form of a cDNA. It is exemplary for every DNA falling under the present invention.

For preparing a cDNA according to the invention, it is favorable to use as a basis a cosmid library which comprises the region Xq28 of the human genome. Such a cosmid library is e.g. the Xq28-specific cosmid library (cf. Kioschis, P. et al., Cytogenet. Cell. Genet. 58, (1991), 2070) which was prepared from the cell hybrid QIZ (cf. Warren, S. T. et al., Proc. Natl. Acad. Scif U.S.A. 87 (1990), 3856–3860). The cosmid clones Qc8D11, Qc3F12 and Qc12G11 thereof (cf. Kioschis, P. et al., Cytogenet. Cell. Genet. 58, (1991), 2070; Kioschis, P. et al., Genomics 33, (1996) in print) are used and subjected to DNA selection (cf. Korn, B. et al., Mol. Genet. 4 (1992), 235–242) s o as to obtain the cDNA fragment 79g1P5. It is used for hybridizing a cDNA library of human placenta (e.g. STRATAGENE, catalog No. 936203). A cDNA according to the invention is obtained.

A cDNA according to the invention may be present in a vector and expression vector, respectively. A person skilled in the art is familiar with examples thereof. In the case of an expression vector for *E. coli* these are e.g. pGEMEX, pUC derivatives, pGEX-2T, pET3b and pQE-8, the latter being preferred. For the expression in yeast, e.g. pY100 and Ycpad1 have to be mentioned while e.g. pkCR, pEFBOS, cDM8 and pCEV4 have to be indicated for the expression in animal cells . The baculovirus expression vector pAcSGHisNT-A is especially suitable for the expression in insect cells.

The person skilled in the art is familiar with suitable cells to express a cDNA according to the invention, which is present in an expression vector. Examples of such cells comprise the *E. coli* strains RB101, DH1, x1776, JM101, JM109, BL21 and SG13009, the latter being preferred, the yeast strain saccharomyces cerevisiae and the animal cells L, 3T3, FM3A, CHO, COS, Vero and HeLa as well as the insect cells sf9.

The person skilled in the art knows in which way a DNA according to the invention has to be inserted in an expression vector. He is also familiar with the fact that this DNA can be inserted in combination with a DNA coding for another protein and peptide, respectively, so that the cDNA according to the invention can be expressed in the form of a fusion protein.

In addition, the person skilled in the art knows conditions of culturing transformed cells and transfected cells, respectively. He is also familiar with processes of isolating and purifying the protein expressed by the cDNA according to the invention. Thus, such a protein, which may also be a fusion protein, is also a subject matter of the present invention.

A further subject matter of the present invention relates to an antibody directed against an above protein and fusion protein, respectively. Such an antibody can be prepared by common methods. It may be polyclonal and monoclonal, respectively. For its preparation it is favorable to immunize animals—particularly rabbits or chickens for a polyclonal antibody and mice for a monoclonal antibody—with an above (fusion) protein or with fragments thereof. Further "boosters" of the animals can be effected with the same (fusion) protein or with fragments thereof. The polyclonal antibody may then be obtained from the animal serum and egg yolk, respectively. For the preparation of the monoclonal antibody, animal spleen cells are fused with myeloma cells.

The present invention enables to investigate the causes of cell differentiation disturbances, particularly in the case of muscle cells, and more particularly in the case of myotubular myopathy. By means of a nucleic acid according to the invention, particularly a DNA, and primers derived therefrom, it can be determined in mammals, particularly human beings, whether they contain and/or express a gene which codes, within the above sense, for a shortened (TVP) and mutated (TVP), respectively. For this purpose, a person skilled in the art will carry out common methods such as reverse transcription, PCR reaction, hybridization and sequencing. A kit which contains an above nucleic acid, particularly DNA, and/or primers derived therefrom as well as carriers and conventional auxiliary agents, is also provided according to the invention.

Furthermore, the present invention is suited to take therapeutic measures in the case of cell differentiation disturbances, particularly in the case of muscle cells and more particularly in the case of myotubular myopathy. A (TVP) according to the invention can be inserted in mammals, particularly human beings. For this purpose, it may be favorable to couple (TVP) to a protein which is not considered foreign by the respective body, e.g. transferrin or BSA. A nucleic acid according to the invention, particularly a DNA, can also be inserted and expressed in mammals, particularly human beings. For this purpose, it may be favorable to have the expression of the nucleic acid according to the invention be controlled by a tissue-specific promoter, particularly a muscle-specific promoter. The expression of (TVP) can be controlled and regulated by an antibody according to the invention.

Thus, the present invention represents a great contribution to the diagnostic and therapeutic detection of disturbances of cell differentiation, particularly in the case of muscle cells and more particularly in the case of myotubular myopathy. In this connection, the diagnostic detection cannot only be made postnatally but also prenatally already.

BRIEF DESCRIPTION OF THE DRAWING

FIGS. 1A–1E shows the base sequence and the amino acid sequence, derived therefrom, of a (TVP) according to the invention.

The present invention is explained by the below examples.

Example 1

Preparation and Purification of a (TVP) According to the Invention

For preparing a (TVP) according to the invention, the DNA of FIG. 1 was used as a template. A PCR method was carried out. The following primer pair was used:

MTM-F: 5'-CAGGGATCCGATGGCAGCCGAGCAGC CTGGCAAC-3' and MTM-RR: 5'-GGGGGATCCTCAGAAGTGAGTTTGCA CATGGGG-3'

The PCR batch and PCR conditions were as follows:
PCR batch
Template DNA (FIG. 1): 1 μl=1 ng
Pfu polymerase 10x buffer: 10 μl=1 x
DMSO: 10 μl=10 %
dNTP's: 1 μl=200 μM each
oligonucleotides, 1.5 μl each: 3 μl=150 ng each
H₂O bidist.: ad 99 μl PCR conditions
92° C.—5 min.
addition of 1 μl Pfu polymerase (Stratagene)=2.5 units
addition of paraffin

| PCR | | |
|---|---|---|
| 92° C. | 1 min. | |
| 58° C. | 1 min. | 1 cycle |
| 72° C. | 10 min. | |
| 92° C. | 1 min. | |
| 58° C. | 1 min. | 39 cycles |
| 72° C. | 2 min. | |
| 72° C. | 10 min. | 1 cycle |

The amplified DNA was cleaved by Bam HI each and inserted in the expression vector pQE8 (Diagen company) cleaved by Bam HI. The expression plasmid pQ/TVP was obtained. Such a plasmid codes for a fusion protein comprising 6 histidine residues (N terminus partner) and the (TVP) of FIG. 1 according to the invention (C terminus partner). pQ/TVP was used for transforming E. coli SG 13009 (cf. Gottesman, S. et al., J. Bacteriol. 148, (1981), 265–273). The bacteria were cultured in an LB broth with 100 μg/ml ampicillin and 25 μg/ml kanamycin and induced with 60 μM isopropyl-β-D-thiogalactopyranoside (IPTG) for 4 h. Lysis of the bacteria was achieved by the addition of 6 M guanidine hydrochloride. Thereafter, chromatography (Ni-NTA resin) was carried out with the lysate in the presence of 8 M urea in accordance with the instructions from the manufacturer (Diagen company) of the chromatography material. The bound fusion protein was eluted in a buffer having a pH of 3.5. After its neutralization, the fusion protein was subjected to 18 % SDS polyacrylamide gel electrophoresis and stained with coomassie blue (cf. Thomas, J. O. and Kornberg, R. D., J. Mol. Biol. 149 (1975), 709–733).

It showed that a (fusion) protein according to the invention can be prepared in highly pure form.

Example 2

Preparation and Detection of an Antibody According to the Invention

A fusion protein of Example 1 according to the invention was subjected to 18 SDS polyacrylamide gel electrophoresis. After staining the gel with 4 M sodium acetate, an about 205 kD band was cut out of the gel and incubated in phosphate-buffered common salt solution. Gel pieces were sedimented before the protein concentration of the supernatant was determined by SDS polyacrylamide gel electrophoresis which was followed by coomassie blue staining. Animals were immunized with the gel-purified fusion protein as follows:

Immunization Protocol for Polyclonal Antibodies in Rabbits
35 μg of gel-purified fusion protein in 0.7 ml PBS and 0.7 ml of complete Freund's adjuvant and incomplete Freund's adjuvant, respectively, were used per immunization:

Day 0: 1$^{st}$ immunization (complete Freund's adjuvant)
Day 14: 2$^{nd}$ immunization (incomplete Freund's adjuvant; icFA)
Day 28: 3$^{rd}$ immunization (icFA)
Day 56: 4$^{th}$ immunization (icFA)
Day 80: bleeding to death.

The rabbit serum was tested in an immunoblot. For this purpose, a fusion protein of Example 1 according to the invention was subjected to SDS polyacrylamide gel electrophoresis and transferred to a nitrocellulose filter (cf. Khyse-Andersen, J., J. Biochem. Biophys. Meth. 10 (1984), 203–209). The Western blot analysis was carried out as described in Bock, C.-T. et al., Virus Genes 8, (1994), 215–229. For this purpose, the nitrocellulose filter was incubated with a first antibody at 37° C. for one hour. This antibody was the rabbit serum (1:10000 in PBS). After several wash steps using PBS, the nitrocellulose filter was incubated with a second antibody. This antibody was an alkaline phosphatase-coupled monoclonal goat anti-rabbit IgG antibody (Dianova company) (1:5000) in PBS. 30 minutes of incubation at 37° C. were followed by several wash steps using PBS and subsequently by the alkaline phosphatase detection reaction with developer solution (36 µM 5'-bromo-4-chloro-3-indolylphosphate, 400 µM nitro blue tetrazolium, 100 mM Tris-HCl, pH 9.5, 100 mM NaCl, 5 mM $MgCl_2$) at room temperature until bands were visible.

It showed that polyclonal antibodies according to the invention can be prepared.

Immunization Protocol for Polyclonal Antibodies in Chickens

40 µg of gel-purified fusion protein in 0.8 ml PBS and 0.8 ml of complete Freund's adjuvant and incomplete Freund's adjuvant, respectively, were used per immunization.

Day 0: $1^{st}$ immunization (complete Freund's adjuvant)

Day 28: $2^{nd}$ immunization (incomplete Freund's adjuvant; icFA)

Day 50: $3^{rd}$ immunization (icFA)

Antibodies were extracted from egg yolk and tested in a Western blot. Polyclonal antibodies according to the invention were detected.

Immunization Protocol for Monoclonal Antibodies in Mice

12 µg of gel-purified fusion protein in 0.25 ml PBS and 0.25 ml of complete Freund's adjuvant and incomplete Freund's adjuvant, respectively, were used per immunization. The fusion protein was dissolved in 0.5 ml (without adjuvant) in the $4^{th}$ immunization.

Day 0: $1^{st}$ immunization (complete Freund's adjuvant)

Day 28: $2^{nd}$ immunization (incomplete Freund's adjuvant; icFA)

Day 56: $3^{rd}$ immunization (icFA)

Day 84: $4^{th}$ immunization (PBS)

Day 87: fusion.

Supernatants of hybridomas were tested in a Western blot. Monoclonal antibodies according to the invention were detected.

What is claimed is:

1. A purified tyrosine phosphatase-related protein, comprising the amino acid sequence of FIG. 1 (SEQ ID NO:2) or an amino acid sequence differing therefrom by one or several amino acids, wherein the DNA encoding the latter amino acid sequence hybridizes completely with tie DNA of FIG. 1 (SEQ ID NO:1) at 20° C. below the melting point of the DNA, and wherein the protein disturbs the differentiation of muscle cells.

2. An isolated DNA encoding the protein according to claim 1, wherein the DNA comprises;
   (a) the DNA of FIG. 1 (SEQ ID NO:1) or a DNA differing therefrom by one or several base pairs, the latter DNA completely hybridizing with the DNA of FIG. 1 (SEQ ID NO:1) at 20° C. below the melting point of the DNA, or
   b) a DNA related to the DNA of (a) via the degeneracy of the genetic code.

3. An expression plasmid, comprising the DNA according to claim 2.

4. A transformant comprising the expression plasmid according to claim 3.

5. A process for the preparation of the protein according to claim 1, wherein said process comprises culturing a transformant containing a expression plasmid comprising:
   (a) the DNA of FIG. 1 (SEQ ID NO:1) or a DNA differing therefrom by one or several base pairs, the latter DNA completely hybridizing with the DNA of FIG. 1 (SEQ ID NO:1) at 20° C. below the melting point of the DNA, or
   (b) a DNA related to the DNA of (a) via the degeneracy of the genetic code.

6. A reagent for treating disturbed cell differentiation comprising the protein according to claim 1.

7. The reagent according to claim 6, wherein said disturbed cell differentiation is myotubular myopathy.

8. A reagent for the diagnosis and/or treatment of disturbed cell differentiation comprising the DNA according to claim 2.

9. The reagent according to claim 8, wherein said disturbed cell differentiation is myotubular myopathy.

* * * * *

SEQUENCE LISTING

```
<160> NUMBER OF SEQ ID NOS: 4

<210> SEQ ID NO 1
<211> LENGTH: 3431
<212> TYPE: DNA
<213> ORGANISM: German-type microorganism & cell cul.
<220> FEATURE:
<221> NAME/KEY: CDS
<222> LOCATION: (1)..(1863)

<400> SEQUENCE: 1 gca gcc gag cag cct ggc aac ggc ggt ggc gcc cgg agc ccg aga gtt      48
Ala Ala Glu Gln Pro Gly Asn Gly Gly Gly Ala Arg Ser Pro Arg Val
  1               5                  10                  15 tcc agg atg gct tct gca tca act tct aaa tat aat tca cac tcc ttg      96
Ser Arg Met Ala Ser Ala Ser Thr Ser Lys Tyr Asn Ser His Ser Leu
             20                  25                  30 gag aat gag tct att aag agg acg tct cga gat gga gtc aat cga gat     144
Glu Asn Glu Ser Ile Lys Arg Thr Ser Arg Asp Gly Val Asn Arg Asp
         35                  40                  45 ctc act gag gct gtt cct cga ctt cca gga gaa aca cta atc act gac     192
Leu Thr Glu Ala Val Pro Arg Leu Pro Gly Glu Thr Leu Ile Thr Asp
     50                  55                  60 aaa gaa gtt att tac ata tgt cct ttc aat ggc ccc att aag gga aga     240
Lys Glu Val Ile Tyr Ile Cys Pro Phe Asn Gly Pro Ile Lys Gly Arg
 65                  70                  75                  80 gtt tac atc aca aat tat cgt ctt tat tta aga agt ttg gaa acg gat     288
Val Tyr Ile Thr Asn Tyr Arg Leu Tyr Leu Arg Ser Leu Glu Thr Asp
                 85                  90                  95 tct tct cta ata ctt gat gtt cct ctg ggt gtg atc tcg aga att gaa     336
Ser Ser Leu Ile Leu Asp Val Pro Leu Gly Val Ile Ser Arg Ile Glu
            100                 105                 110 aaa atg gga ggc gcg aca agt aga gga gaa aat tcc tat ggt cta gat     384
Lys Met Gly Gly Ala Thr Ser Arg Gly Glu Asn Ser Tyr Gly Leu Asp
        115                 120                 125
```

-continued

```
att act tgt aaa gac atg aga aac ctg agg ttc gct ttg aaa cag gaa    432
Ile Thr Cys Lys Asp Met Arg Asn Leu Arg Phe Ala Leu Lys Gln Glu
        130                 135                 140 ggc cac agc aga aga gat atg ttt gag atc ctc acg aga tac gcg ttt    480
Gly His Ser Arg Arg Asp Met Phe Glu Ile Leu Thr Arg Tyr Ala Phe
145                 150                 155                 160 ccc ctg gct cac agt ctg cca tta ttt gca ttt tta aat gaa gaa aag    528
Pro Leu Ala His Ser Leu Pro Leu Phe Ala Phe Leu Asn Glu Glu Lys
                165                 170                 175 ttt aac gtg gat gga tgg aca gtt tac aat cca gtg gaa gaa tac agg    576
Phe Asn Val Asp Gly Trp Thr Val Tyr Asn Pro Val Glu Glu Tyr Arg
            180                 185                 190 agg cag ggc ttg ccc aat cac cat tgg aga ata act ttt att aat aag    624
Arg Gln Gly Leu Pro Asn His His Trp Arg Ile Thr Phe Ile Asn Lys
        195                 200                 205 tgc tat gag ctc tgt gac act tac cct gct ctt ttg gtg gtt ccg tat    672
Cys Tyr Glu Leu Cys Asp Thr Tyr Pro Ala Leu Leu Val Val Pro Tyr
    210                 215                 220 cgt gcc tca gat gat gac ctc cgg aga gtt gca act ttt agg tcc cga    720
Arg Ala Ser Asp Asp Asp Leu Arg Arg Val Ala Thr Phe Arg Ser Arg
225                 230                 235                 240 aat cga att cca gtg ctg tca tgg att cat cca gaa aat aag acg gtc    768
Asn Arg Ile Pro Val Leu Ser Trp Ile His Pro Glu Asn Lys Thr Val
                245                 250                 255 att gtg cgt tgc agt cag cct ctt gtc ggt atg agt ggg aaa cga aat    816
Ile Val Arg Cys Ser Gln Pro Leu Val Gly Met Ser Gly Lys Arg Asn
            260                 265                 270 aaa gat gat gag aaa tat ctc gat gtt atc agg gag act aat aaa caa    864
Lys Asp Asp Glu Lys Tyr Leu Asp Val Ile Arg Glu Thr Asn Lys Gln
        275                 280                 285 att tct aaa ctc acc att tat gat gca aga ccc agc gta aat gca gtg    912
Ile Ser Lys Leu Thr Ile Tyr Asp Ala Arg Pro Ser Val Asn Ala Val
    290                 295                 300 gcc aac aag gca aca gga gga gga tat gaa agt gat gat gca tat cat    960
Ala Asn Lys Ala Thr Gly Gly Gly Tyr Glu Ser Asp Asp Ala Tyr His
305                 310                 315                 320 aac gcc gaa ctt ttc ttc tta gac att cat aat att cat gtt atg cgg   1008
Asn Ala Glu Leu Phe Phe Leu Asp Ile His Asn Ile His Val Met Arg
                325                 330                 335 gaa tct tta aaa aaa gtg aag gac att gtt tat cct aat gta gaa gaa   1056
Glu Ser Leu Lys Lys Val Lys Asp Ile Val Tyr Pro Asn Val Glu Glu
            340                 345                 350 tct cat tgg ttg tcc agt ttg gag tct act cat tgg tta gaa cat atc   1104
Ser His Trp Leu Ser Ser Leu Glu Ser Thr His Trp Leu Glu His Ile
        355                 360                 365 aag ctc gtt ttg aca gga gcc att caa gta gca gac aaa gtt tct tca   1152
Lys Leu Val Leu Thr Gly Ala Ile Gln Val Ala Asp Lys Val Ser Ser
    370                 375                 380 ggg aag agt tca gtg ctt gtg cat tgc agt gac gga tgg gac agg act   1200
Gly Lys Ser Ser Val Leu Val His Cys Ser Asp Gly Trp Asp Arg Thr
385                 390                 395                 400 gct cag ctg aca tcc ttg gcc atg ctg atg ttg gat agc ttc tat agg   1248
Ala Gln Leu Thr Ser Leu Ala Met Leu Met Leu Asp Ser Phe Tyr Arg
                405                 410                 415 agc att gaa ggg ttc gaa ata ctg gta caa aaa gaa tgg ata agt ttt   1296
Ser Ile Glu Gly Phe Glu Ile Leu Val Gln Lys Glu Trp Ile Ser Phe
            420                 425                 430 gga cat aaa ttt gca tct cga ata ggt cat ggt gat aaa aac cac acc   1344
Gly His Lys Phe Ala Ser Arg Ile Gly His Gly Asp Lys Asn His Thr
        435                 440                 445
```

-continued

```
gat gct gac cgt tct cct att ttt ctc cag ttt att gat tgt gtg tgg     1392
Asp Ala Asp Arg Ser Pro Ile Phe Leu Gln Phe Ile Asp Cys Val Trp
    450                 455                 460 caa atg tca aaa cag ttc cct aca gct ttt gaa ttc aat gaa caa ttt     1440
Gln Met Ser Lys Gln Phe Pro Thr Ala Phe Glu Phe Asn Glu Gln Phe
465                 470                 475                 480 ttg att ata att ttg gat cat ctg tat agt tgc cga ttt ggt act ttc     1488
Leu Ile Ile Ile Leu Asp His Leu Tyr Ser Cys Arg Phe Gly Thr Phe
                485                 490                 495 tta ttc aac tgt gaa tct gct cga gaa aga cag aag gtt aca gaa agg     1536
Leu Phe Asn Cys Glu Ser Ala Arg Glu Arg Gln Lys Val Thr Glu Arg
                500                 505                 510 act gtt tct tta tgg tca ctg ata aac agt aat aaa gaa aaa ttc aaa     1584
Thr Val Ser Leu Trp Ser Leu Ile Asn Ser Asn Lys Glu Lys Phe Lys
            515                 520                 525 aac ccc ttc tat act aaa gaa atc aat cga gtt tta tat cca gtt gcc     1632
Asn Pro Phe Tyr Thr Lys Glu Ile Asn Arg Val Leu Tyr Pro Val Ala
        530                 535                 540 agt atg cgt cac ttg gaa ctc tgg gtg aat tac tac att aga tgg aac     1680
Ser Met Arg His Leu Glu Leu Trp Val Asn Tyr Tyr Ile Arg Trp Asn
545                 550                 555                 560 ccc agg atc aag caa caa cag ccg aat cca gtg gag cag cgt tac atg     1728
Pro Arg Ile Lys Gln Gln Gln Pro Asn Pro Val Glu Gln Arg Tyr Met
                565                 570                 575 gag ctc tta gcc tta cgc gac gaa tac ata aag cgg ctt gag gaa ctg     1776
Glu Leu Leu Ala Leu Arg Asp Glu Tyr Ile Lys Arg Leu Glu Glu Leu
                580                 585                 590 cag ctc gcc aac tct gcc aag ctt tct gat ccc cca act tca cct tcc     1824
Gln Leu Ala Asn Ser Ala Lys Leu Ser Asp Pro Pro Thr Ser Pro Ser
            595                 600                 605 agt cct tcg caa atg atg ccc cat gtg caa act cac ttc tgaggggga      1873
Ser Pro Ser Gln Met Met Pro His Val Gln Thr His Phe
        610                 615                 620 ccctggcacc gcattagagc tcgaaataaa ggcgatagct gactttcatt tgggcattt   1933 gtaaaaagta gattaaaata tttgcctcca tgtagaactt gaactaacat aatcttaaac   1993
tcttgaatat gtgccttcta gaatacatat tacaagaaaa ctacagggtc cacacggcaa   2053
tcagaagaaa ggagctgaga tgaggttttg gaaaaccctg acacctttaa aaagcagttt   2113
ttgaaagaca aaatttagat ttaatttacg tcttgagaaa tactatatat acaatatata   2173 tgggggggc ttaattgaaa caacattatt ttaaaatcaa aggggatata tgtttgtgga   2233
tggattttcc tgaagctgca ttaacagttg cttttggattc tctaagatga atccaaatgt   2293
gaaagatgca tgttactgcc aaaaccaaat tgagctcagc ttcctaggca ttacccaaaa   2353
gcaaggtgtt taagtaattg ccagctttta taccatcatg agtggtgact taaggagaaa   2413
tagctgtata gatgagtttt tcattatttg gaaatttagg ggtagaaaat gttttcccct   2473
aattttccag agaagcctat tttatatttt ttaaaaaact gacagggccc agttaaatat   2533
gatttgcatt tttaaatttt gccagttta ttttctaaat tctttcatga gcttgcctaa   2593
aattcggaat ggttttcggg ttgtggcaaa ccccaaagag agcactgtcc aaggatgtcg   2653
ggagcatcct gctgcttagg ggaatgtttt cgcaaatgtt gctctagtca gtccagctca   2713
tctgccaaaa tgtagggcta ccgtcttgga tgcatgagct attgctagag catcatcctt   2773
agaaatcagt gccccagatg tacatgtgtt gagcgtattc ttgaagtatt gtgtttatgc   2833
atttcaattt caatggtgtt ggcttcccct ccccacccca cgcgtgcata aaaactggtt   2893
```

-continued

```
ctacaaattt ttacttgaag taccaggccg tttgctttt caggttgttt tgttttatag    2953
tattaagtga aattttaaat gcacagttct atttgctatc tgaactaatt catttattaa    3013
gtatatttgt aaaagctaag gctcgagtta aacaatgaa gtgttttaca atgatttgta    3073
aaggactatt tataactaat atggttttgt tttcaatgaa ttaagaaaga ttaaatatat    3133
ctttgtaaat tattttatgt catagttaat tggtctccca agtaagacat ctcaaataca    3193
gtagtataat gtatgaattt tgtaagtata agaaatttta ttagacattc tcttactttt    3253
tgtaaatgct gtaaatattt cataaattaa caaagtgtca ctccataaaa agaaagctaa    3313
tactaatagc ctaaaagatt ttgtgaaatt tcatgaaaac tttttaatgg caataatgac    3373
taaagacctg ctgtaataaa tgtattaact gaaacctaaa aaaaaaaaaa aaaaaaa      3431
```

<210> SEQ ID NO 2
<211> LENGTH: 621
<212> TYPE: PRT
<213> ORGANISM: German-type microorganism & cell cul.

<400> SEQUENCE: 2

```
Ala Ala Glu Gln Pro Gly Asn Gly Gly Ala Arg Ser Pro Arg Val
 1               5                  10                  15

Ser Arg Met Ala Ser Ala Ser Thr Ser Lys Tyr Asn Ser His Ser Leu
                20                  25                  30

Glu Asn Glu Ser Ile Lys Arg Thr Ser Arg Asp Gly Val Asn Arg Asp
             35                  40                  45

Leu Thr Glu Ala Val Pro Arg Leu Pro Gly Glu Thr Leu Ile Thr Asp
         50                  55                  60

Lys Glu Val Ile Tyr Ile Cys Pro Phe Asn Gly Pro Ile Lys Gly Arg
 65                  70                  75                  80

Val Tyr Ile Thr Asn Tyr Arg Leu Tyr Leu Arg Ser Leu Glu Thr Asp
                 85                  90                  95

Ser Ser Leu Ile Leu Asp Val Pro Leu Gly Val Ile Ser Arg Ile Glu
                100                 105                 110

Lys Met Gly Gly Ala Thr Ser Arg Gly Glu Asn Ser Tyr Gly Leu Asp
            115                 120                 125

Ile Thr Cys Lys Asp Met Arg Asn Leu Arg Phe Ala Leu Lys Gln Glu
        130                 135                 140

Gly His Ser Arg Arg Asp Met Phe Glu Ile Leu Thr Arg Tyr Ala Phe
145                 150                 155                 160

Pro Leu Ala His Ser Leu Pro Leu Phe Ala Phe Leu Asn Glu Glu Lys
                165                 170                 175

Phe Asn Val Asp Gly Trp Thr Val Tyr Asn Pro Val Glu Glu Tyr Arg
            180                 185                 190

Arg Gln Gly Leu Pro Asn His His Trp Arg Ile Thr Phe Ile Asn Lys
        195                 200                 205

Cys Tyr Glu Leu Cys Asp Thr Tyr Pro Ala Leu Leu Val Val Pro Tyr
    210                 215                 220

Arg Ala Ser Asp Asp Leu Arg Arg Val Ala Thr Phe Arg Ser Arg
225                 230                 235                 240

Asn Arg Ile Pro Val Leu Ser Trp Ile His Pro Glu Asn Lys Thr Val
                245                 250                 255

Ile Val Arg Cys Ser Gln Pro Leu Val Gly Met Ser Gly Lys Arg Asn
            260                 265                 270

Lys Asp Asp Glu Lys Tyr Leu Asp Val Ile Arg Glu Thr Asn Lys Gln
        275                 280                 285
```

```
Ile Ser Lys Leu Thr Ile Tyr Asp Ala Arg Pro Ser Val Asn Ala Val
    290                 295                 300

Ala Asn Lys Ala Thr Gly Gly Tyr Glu Ser Asp Ala Tyr His
305                 310                 315                 320

Asn Ala Glu Leu Phe Phe Leu Asp Ile His Asn Ile His Val Met Arg
                325                 330                 335

Glu Ser Leu Lys Lys Val Lys Asp Ile Val Tyr Pro Asn Val Glu Glu
                340                 345                 350

Ser His Trp Leu Ser Ser Leu Glu Ser Thr His Trp Leu Glu His Ile
            355                 360                 365

Lys Leu Val Leu Thr Gly Ala Ile Gln Val Ala Asp Lys Val Ser Ser
    370                 375                 380

Gly Lys Ser Ser Val Leu Val His Cys Ser Asp Gly Trp Asp Arg Thr
385                 390                 395                 400

Ala Gln Leu Thr Ser Leu Ala Met Leu Met Leu Asp Ser Phe Tyr Arg
                405                 410                 415

Ser Ile Glu Gly Phe Glu Ile Leu Val Gln Lys Glu Trp Ile Ser Phe
                420                 425                 430

Gly His Lys Phe Ala Ser Arg Ile Gly His Gly Asp Lys Asn His Thr
            435                 440                 445

Asp Ala Asp Arg Ser Pro Ile Phe Leu Gln Phe Ile Asp Cys Val Trp
    450                 455                 460

Gln Met Ser Lys Gln Phe Pro Thr Ala Phe Glu Phe Asn Glu Gln Phe
465                 470                 475                 480

Leu Ile Ile Ile Leu Asp His Leu Tyr Ser Cys Arg Phe Gly Thr Phe
                485                 490                 495

Leu Phe Asn Cys Glu Ser Ala Arg Glu Arg Gln Lys Val Thr Glu Arg
                500                 505                 510

Thr Val Ser Leu Trp Ser Leu Ile Asn Ser Asn Lys Glu Lys Phe Lys
            515                 520                 525

Asn Pro Phe Tyr Thr Lys Glu Ile Asn Arg Val Leu Tyr Pro Val Ala
    530                 535                 540

Ser Met Arg His Leu Glu Leu Trp Val Asn Tyr Tyr Ile Arg Trp Asn
545                 550                 555                 560

Pro Arg Ile Lys Gln Gln Pro Asn Pro Val Glu Gln Arg Tyr Met
                565                 570                 575

Glu Leu Leu Ala Leu Arg Asp Glu Tyr Ile Lys Arg Leu Glu Glu Leu
                580                 585                 590

Gln Leu Ala Asn Ser Ala Lys Leu Ser Asp Pro Thr Ser Pro Ser
            595                 600                 605

Ser Pro Ser Gln Met Met Pro His Val Gln Thr His Phe
    610                 615                 620

<210> SEQ ID NO 3
<211> LENGTH: 34
<212> TYPE: DNA
<213> ORGANISM: German-type microorganism & cell cul.

<400> SEQUENCE: 3
cagggatccg atggcagccg agcagcctgg caac                         34

<210> SEQ ID NO 4
<211> LENGTH: 33
<212> TYPE: DNA
<213> ORGANISM: German-type microorganism & cell cul.
```

```
-continued

<400> SEQUENCE: 4
gggggatcct cagaagtgag tttgcacatg ggg                                  33
```